United States Patent [19]

Stucki-McCormick

[11] Patent Number: 5,961,329
[45] Date of Patent: Oct. 5, 1999

[54] COMBINATION DISTRACTION DENTAL IMPLANT AND METHOD OF USE

[76] Inventor: Suzanne U. Stucki-McCormick, 525 E. 72nd St., New York, N.Y. 10021

[21] Appl. No.: 08/886,078

[22] Filed: Jul. 2, 1997

[51] Int. Cl.$^6$ .................................................. A61C 8/00
[52] U.S. Cl. ............................................ 433/173; 433/174
[58] Field of Search ................................... 433/172, 173, 433/174

[56] References Cited

U.S. PATENT DOCUMENTS

| D. 294,295 | 2/1988 | Branemark | D24/33 |
|---|---|---|---|
| 3,547,113 | 12/1970 | Swanson | 128/84 |
| 4,011,602 | 3/1977 | Rybicki et al. | 3/1.9 |
| 4,096,857 | 6/1978 | Cramer et al. | 128/84 |
| 4,187,841 | 2/1980 | Knutson | 128/92 |
| 4,330,891 | 5/1982 | Branemark et al. | 3/1 |
| 4,552,532 | 11/1985 | Mozsary | 433/173 |
| 4,657,510 | 4/1987 | Gittleman | 433/173 |
| 4,682,951 | 7/1987 | Linkow | 433/173 |
| 4,798,205 | 1/1989 | Bonomo et al. | 128/344 |
| 4,824,372 | 4/1989 | Jorneus et al. | 433/174 |
| 4,872,840 | 10/1989 | Bori | 433/173 |
| 4,880,006 | 11/1989 | Albrektsson et al. | 128/630 |
| 4,915,628 | 4/1990 | Linkow et al. | 433/173 |
| 4,929,247 | 5/1990 | Rayhack | 606/53 |
| 4,960,381 | 10/1990 | Niznick | 433/174 |
| 5,064,374 | 11/1991 | Lundgren | 433/173 |
| 5,064,425 | 11/1991 | Branemark et al. | 606/72 |
| 5,069,622 | 12/1991 | Rangert et al. | 433/173 |
| 5,098,293 | 3/1992 | Loof et al. | 433/165 |
| 5,100,323 | 3/1992 | Friedman et al. | 433/173 |
| 5,125,841 | 6/1992 | Carlsson et al. | 433/213 |
| 5,145,371 | 9/1992 | Jorneus et al. | 433/173 |
| 5,154,612 | 10/1992 | Carlsson et al. | 433/173 |
| 5,259,759 | 11/1993 | Jorneus et al. | 433/173 |
| 5,269,685 | 12/1993 | Jorneus et al. | 433/174 |
| 5,281,140 | 1/1994 | Niznick | 433/172 |
| 5,334,024 | 8/1994 | Niznick | 433/173 |
| 5,364,396 | 11/1994 | Robinson et al. | 606/53 |
| 5,378,152 | 1/1995 | Elia | 433/173 |
| 5,449,291 | 9/1995 | Lueschen et al. | 433/173 |
| 5,470,230 | 11/1995 | Daftary et al. | 433/174 |

(List continued on next page.)

FOREIGN PATENT DOCUMENTS

| 404 094 | 1/1998 | Austria . |
| 0446191 | 11/1991 | European Pat. Off. . |
| 0747017 | 11/1996 | European Pat. Off. . |

OTHER PUBLICATIONS

Osteodistraction–McCormick, Suzanne U.–Selected Readings In Oral and Maxillofacial Surgury–vol. 4, No. 7–University of Texas Southwestern Medical Center at Dallas.

*Primary Examiner*—John J. Wilson
*Attorney, Agent, or Firm*—Levisohn, Lerner, Berger & Langsam

[57] ABSTRACT

A combination distraction device and methods of using are disclosed. The combination distraction device comprises a two component portion (an apical and a coronal component) and an expansion component for separating the two components once the device has been initially integrated into the bone. Internal threads of the apical and the coronal components are adapted to operatively cooperating with the threads of the expansion component such that the distance between the apical component and the coronal component is selectively varied. When assembled, the expansion component is advanced into the two separable components by rotating, for example, the expansion component in a clockwise direction. As the expansion component is advanced into the two component portion of the combination distraction dental implant, one end of the expansion component engages the end of the internal thread in the apical component, causing separation between the apical and coronal components thereby forming a gap. Since, when placed in a patient, the apical and coronal components become integrated, fused intra-osseously to the bone, separating these two components expands a distraction gap previously made in the bone proximal the separation point between the two components and provides for the formation of new bone and soft tissue.

52 Claims, 8 Drawing Sheets

U.S. PATENT DOCUMENTS

| | | | |
|---|---|---|---|
| 5,489,210 | 2/1996 | Hanosh | 433/173 |
| 5,505,733 | 4/1996 | Justin et al. | 606/63 |
| 5,540,687 | 7/1996 | Fairley et al. | 606/60 |
| 5,571,016 | 11/1996 | Ingber et al. | 433/173 |
| 5,584,694 | 12/1996 | Forsmalm et al. | 433/172 |
| 5,593,444 | 1/1997 | Svensson et al. | 623/16 |
| 5,599,183 | 2/1997 | Razdolsky et al. | 433/53 |
| 5,622,493 | 4/1997 | Razdolsky et al. | 433/7 |
| 5,695,335 | 12/1997 | Haas, et al. | 433/173 |

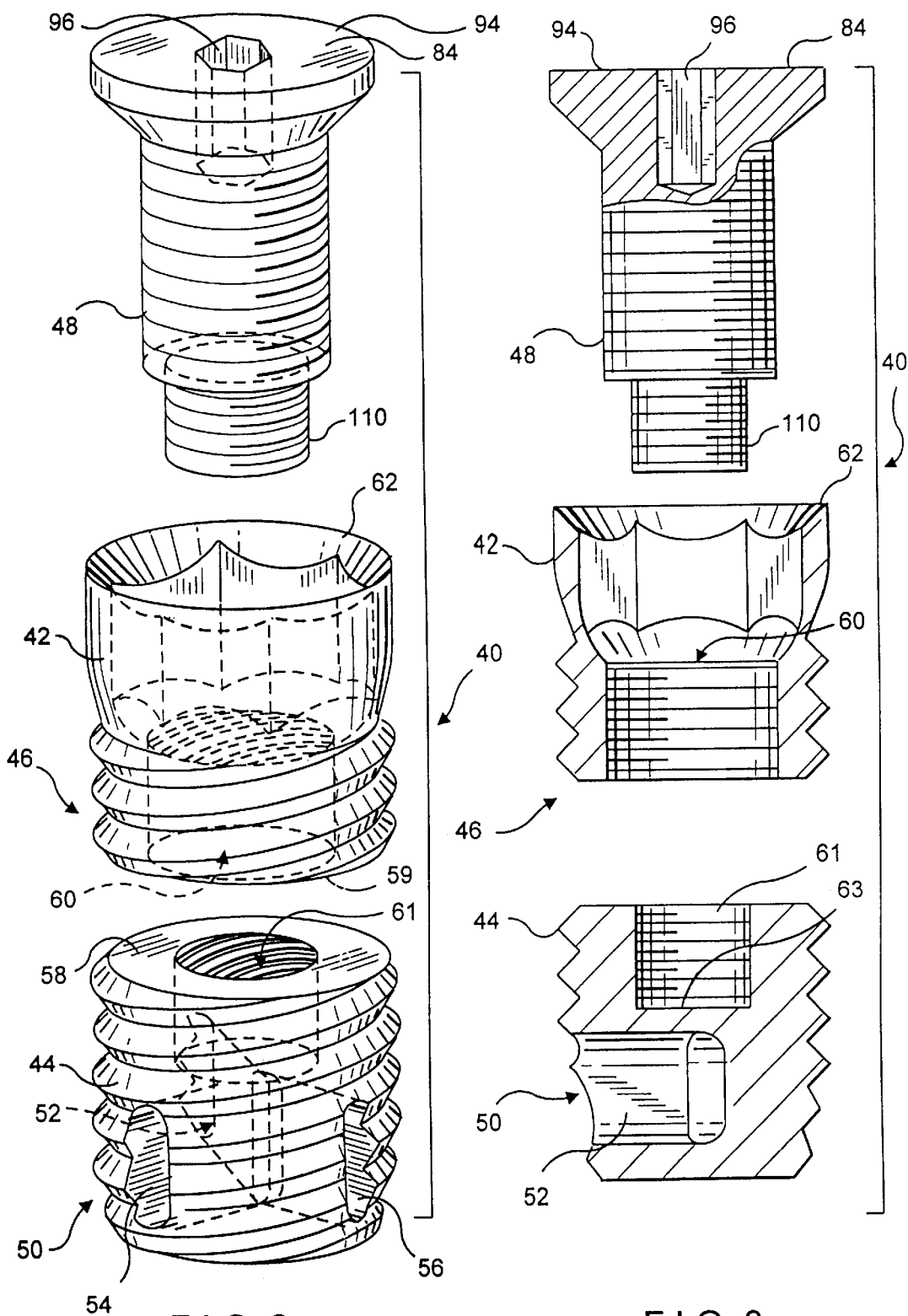

COMBINATION DISTRACTION DENTAL IMPLANT AND METHOD OF USE

BACKGROUND OF THE INVENTION

The present invention relates generally to dental implant systems and methods for replacing missing teeth with dental implants, more particularly, to dental implant systems and surgical methods for replacing teeth with dental implants in areas of the mouth that have suffered bone loss and most particularly to combination distraction dental implant devices and methods for replacing missing teeth in areas of the jaw bone having bone loss using a three component combination distraction dental implant device including two cylindrical like components and a connecting third component or an expansion third component to grow new bone and soft tissue by distraction osteogenesis.

Premature tooth loss can limit a patient's ability to chew and speak clearly. Consequently, patients request tooth replacement. In the past, dentists have been able to replace missing teeth by means of removable prosthesis such as partial or complete dentures. Other prior alternatives included the placement of fixed bridge work cemented to adjacent teeth. These two prior methods served only to fill the void of the edentulous space by replacing the crown of the involved teeth but did not replace the root.

Recently, the field of dental implantology has come into its own, as the technology for replacement of the root and the crown portion of the missing teeth has evolved. In dental implantology, the root portion of the missing tooth is replaced first, by surgically implanting a cylindrical root form dental implant into the dentoalveolar bone (Stage I). There are a number of U.S. Patents relating to dental implants, including the following: U.S. Pat. Nos. 5,489,210; 5,470,230; 5,449,291; 5,334,024; 5,281,140; 5,269,685; 5,259,759; 5,154,612; 5,145,371; 5,125,841; 5,069,622; 5,064,425; 5,051,880; 4,960,381; 4,824,372; 4,798,205; 4,682,951; 4,657,510; 4,552,532 and 4,330,891 the disclosure of each is herein incorporated by reference.

As the surgical site heals, the dental implant becomes bonded and incorporated into the surrounding bone forming an integral unit. The dental implant abutment for the creation of the crown of the tooth later, once osseous healing had occurred (4–6 months), is placed at the time of Stage II uncovering.

In some instances, the above is accomplished by a one-stage implant procedure. In the one-stage procedure, also known as the nonsubmerged, either a one-piece fixture, in which the implant and transmucosal portion are fused together, or both an implant body and a healing cap are simultaneously placed. Instead of covering the implant, the soft tissue is sutured around the protruding transmucosal portion or healing cap and left to heal for the same 4 to 6 months. The advantages of one-stage implants is described in detail in an article by Louis F. Clarizio, DDS, entitled "One-stage Implants: An Overview of Their Usefulness and the Techniques for Placement" in the *Postgraduate Dentistry Series*, Volume 3, Number 4, 1996 beginning at page 3, the disclosure of which is hereby incorporated by reference.

Regardless of whether a one-stage or a two-stage implant is used, long term success of dental implants depends upon two factors: (1) the osseous incorporation or integration of the implant with the native bone, and (2) the mechanical loading properties of the prosthetic crown onto the dental implant. Ideally, the longest (13–15 mm) and widest (2.5–5.5 mm) dental implant should be placed in the bone to act as a proper foundation for the tooth crown.

However, as a consequence of premature tooth loss, patients have lost bone in the area of a proposed implant. This bone loss has, in some cases, limited the surgical options, requiring the dentist to place a smaller than optimal sized dental implant. If the dental implant is too small to accommodate the mechanical load from chewing, with time, it will loosen and fail. Thus, the longest and widest implant available, as described above, (based on the bone stock) should be placed. Additionally, due to bone loss or insufficient bone in the implant area, the dental implant may be placed in an anatomical location where the existing bone may not be ideal for prosthetic reconstruction with a crown or bridge, forcing the dentist to replace the missing tooth with a crown that is not as aesthetic or functional as would be considered optimal.

One prior solution to this bone loss problem was to augment the bony bed with the patient's own bone or cadaveric bone as a transplant, or with synthetic bone substitutes. This procedure was done at the time of dental implant placement if the bone loss is not too great. Otherwise the bone augmentation must be done as a first surgical procedure with the placement of the dental implant occurring several months later, as a second surgical procedure, once healing of the bone graft was completed.

Due to the anatomy of the craniofacial region (defined as pertaining to the region of the head which contains the craniofacial bones, including the maxilla, the upper jaw bone includes the bones of the eyes, the hard palate and the nose, and the mandible, the lower jaw bone, usually with reference to specialized surgical or prosthetic reconstructions of this area of the face), augmentation of the deficient bone is not as simple as layering on the transplanted bone and allowing it to heal. Occasionally, the maxillary sinus membrane (located in the upper jaw) must be elevated or the inferior alveolar nerve (located in the lower jaw) transposed to allow room for placement of the bone graft. Regardless of the technique and materials used, the potential morbidity to the patient can be significant.

Another prior technique of producing new bone was that of distraction osteogenesis. Here, the body was "tricked" into making new bone as it attempts to heal a fracture site. Using this technique, the surgeon created an osteotomy or cut in the bone in an area of bone deficiency. As long as a non-critical size gap exists, the body attempts to heal itself by filling in the gap with new bone. If the gap is widened daily, the body recognizes the newly expanded gap and continues to fill the gap with new bone. This results in creation of new bone in the expansion gap. As long as the gap is expanded slowly over time (0.5–2.0 millimeters per day), the body continues to heal the gap, generating new bone.

A critical size defect is one that will not heal on its own i.e. a critical size defect is sufficiently large to allow only for connective tissue healing without bone bridging between the two ends of the defect. A non critical defect is one which will heal on its own by filling in with bone. Each bone of the body has its own "critical size" defect. If a critical size defect exists, then a bone graft or a bone substitute must be placed to allow for osseous regeneration.

Since the native bone is utilized as the template for repair, the new bone generated has the same size and shape as the original bone. This phenomenon of recreating the same size and shape as the original bone is unique to bone generation using distraction osteogenesis and is not accomplished with conventional bone transplantation.

During distraction osteogenesis, in addition to creating new bone, the overlying soft tissues are regenerated, a secondary gain unique to distraction osteogenesis. This secondary beneficial effect has significant clinical implications, for not only is the underlying foundation properly established, but also the overlying soft tissue is recreated providing for aesthetic and functional rehabilitation of the defect.

Distraction osteogenesis defined as the generation of new bone in response to the application of tension stresses placed across an osteotomy site (bone cut site), has been successfully applied to the bones of the maxillofacial region and specifically to the dentoalveolar unit using distraction devices that are external to at least the gums inside the mouth and, in some cases, completely external the mouth. In these prior instances of applying distraction osteogenesis prior to placing a dental implant, an osteotomy (corticotomy) is made in the bone adjacent to the area requiring bone augmentation and one of the prior bone expansion devices was applied. After allowing for a period of initial healing, the prior device was activated by the patient at home, advancing the distraction gap about 0.5 to about 2.0 millimeters a day. For a more complete description of distraction osteogenesis, see the article "Osteodistraction" by the inventor of the present application in *Selected Readings in Oral and Maxillofacial Surgery*, volume 4, Number 7, published by the University of Texas, Southwestern Medical Center at Dallas, in 1996, the disclosure of which is herein incorporated by reference.

After a sufficient amount of new bone matrix was generated, the distraction device was left in place to allow for ossification of the newly generated bone. The prior distraction devices were then removed during a second surgical procedure and dental implant(s) are placed. Once again the patient was required to undergo two surgical procedures: (1) bone generation via distraction osteogenesis and (2) placement of the dental implant.

A minimum of about ten (10) to about fifteen (15) millimeters of bone was required to utilize the existing distraction devices. If there was not enough bone stock to place the existing devices, a bone graft was required prior to the distraction device being placed. In this case, the patient was required to undergo three separate surgical procedures.

The current external and submerged distraction devices are also limited in the amount of bone expansion each device can deliver because they have fixed internal mechanisms which provide for bone expansion from 0.0 mm to the full length specified for a particular device. Presently, for an external distraction device the full length is about 40 mm while for an intraoral distraction device, the full length is about 18 to about 20 mm. Should more bone expansion be required, then a new device was required to be placed during yet another surgical procedure (fourth).

These prior distraction devices took essentially two approaches: (1) the device was situated externally, outside the skin, with pins holding the device in place to the bone, or (2) the device was situated intraorally, inside the mouth, along the gum line, with pins or screws holding the device in place. Devices which are located externally function well but can pose aesthetic concerns while the patient is utilizing the device and also facial scars are created as the pins holding the device in place are moved as the device is activated and the bone is expanded. Intraoral devices do not have as many aesthetic concerns, but are bulky, displacing the lips and cheeks, which can give the patient the appearance of a local infection.

As can be seen above, in the worst case, some patients were required to undergo as many as four (4) separate surgical procedures over a lengthy time period in order to achieve an optimal dental implant. It should be obvious that it is desirable to limit the number of surgical procedure a patient must undergo.

Thus, there is a need for new devices and methods for placing optimally sized dental implants in areas having insufficient bone. Such new devices and methods should reduce the number of surgical procedures a patient must undergo to achieve an optimal implant; should significantly reduce the number of individual distraction devices required for obtaining the appropriate amount of bone in the implant site; should reduce the number of surgical procedures required for placing an optimal implant in the implant site; should incorporate as many features of the prior devices as possible into a combination distraction dental implant device; should reduce patients aesthetic concerns; should reduce, if not totally eliminate, displaced lips and cheeks and should reduce, if not totally eliminate, the need for bone grafts.

SUMMARY OF THE INVENTION

It is accordingly one object of the present application to provide a new combination dental implant and distraction device and method of using which limits the number of surgical procedures a patient must undergo to have an optimum dental implant placed in an area having initially insufficient bone stock.

Another object of the present invention is to provide a combination distraction dental implant device and method of using the device that combines the technology of dental implantology and that of distraction osteogenesis such that a combination distraction dental implant can be utilized as both the bone distraction device and, after the distraction, left in place as the dental implant.

A still further object of the invention is to provide a combination distraction dental implant device that is utilized as the root form for a prosthesis such as, for example, a crown, a bridge or dentures.

Another object of the invention is to provide a combination distraction dental implant that eliminates the need for the complete removal of the distraction device prior to placement of a separate dental implant during another surgical procedure.

A further object of the present invention is to provide a combination distraction dental implant that eliminates the need for bone grafts in areas of limited bone stock in order to place optimal dental implants.

Another object of the invention is to provide a combination distraction dental implant that lifts the sinus during the distraction process.

The above and other objects of the present invention are realized by combining the technology of dental implantology and that of distraction osteogenesis to produce a combination distraction dental implant which serves as both the implant and the distraction device. In preferred embodiments and methods of the present invention, a combination distraction dental implant is utilized as both the distraction or bone expansion device and the dental implant device and is left in place after distraction in the place of the prior conventional dental implant.

One representative embodiment of a specific combination distraction dental implant comprises: a hollow coronal component; a partially hollow apical component initially having at least one surface contiguous with at least one surface of the hollow coronal component; and at least one expansion component for: (a) operatively connecting the hollow coronal component and the partially hollow apical component, and (b) controllably expanding the distance between the contiguous surfaces of the hollow coronal component and the partially hollow apical component to form a gap.

Another representative embodiment of a specific combination distraction dental implant for placing an optimum dental implant in an area having initially insufficient bone stock comprises: a hollow coronal component; a partially hollow apical component operatively positioned proximal the hollow coronal component; and a removable connecting component operatively connecting the hollow coronal component and the partially hollow apical component.

One representative method of the present invention includes the steps of: providing a three component distraction device including a hollow coronal component, a partially hollow apical component and a linking component or a first expansion component; placing the combination distraction device in a predetermined site where bone regeneration is required; allowing the combination distraction device to become integrated into the bone; ensuring that osseous incorporation of the combination distraction device into the bone has been accomplished; performing a corticotomy in the buccal bone at the level of the contiguous surfaces of two of the three components of the combination distraction device to form a distraction gap; educating the patient as to the care and activation of the three component combination distraction device; after allowing for a period of initial healing, maneuvering the connecting component thereby separating the coronal component and the apical component to widen the distraction gap in the bone.

Another representative embodiment of a more general purpose distraction device of the present invention includes: a first component selectively operatively removably connectable to a first predetermined portion of a bone; a second component selectively operatively removably connectable to a second predetermined portion of the bone, the second component being operatively positioned proximal the first component; and a connecting component for: (a) operatively connecting the first and the second components, and (b) controllably expanding the distance between the first and the second components.

Other objects and advantages of the present application will become apparent from the following description, the accompanying drawings and the appended claims.

BRIEF DESCRIPTION OF THE DRAWINGS

FIG. 2 is an exploded view a representative combination distraction dental implant of the present invention with parts shown in phantom;

FIG. 3 is an exploded cross-sectional view of the representative combination distraction dental implant of FIG. 2;

DETAILED DESCRIPTION OF THE INVENTION

The science and technology of dental implants have been described above. As such, dental implants have evolved from a simple cylindrical form to now having external threads, self tapping grooves, vertical grooves, vents, apical holes and treads, and surface coatings/treatments (titanium plasma spray, acid-etch, hydroxylapatite, microspheres, sintered pores, bone promoting substances, selective surface combinations), etc., all of which act to serve as mechanisms to facilitate placement and promote bone healing, thus increasing retention of the implant within the bone. As is known, dental implants can be made of various grades of titanium (Grade I–IV) to increase the strength of the implant itself. Implants may also be stepped or tapered apically, allowing for placement into narrow anatomical spaces. Implants may have a smooth collar to provide for cervical healing. Implants may have external or internal hexagonal, octagonal, spline and other designs to allow for increased retention and anti-rotation, friction-fit/interference-fit of the prosthesis such as, for example, a crown, a bridge or dentures onto the implant. Regardless of the specific manufactures design, a dental implant serves to replace the missing root shape of the tooth, utilizing the best mechanical form available for that manufacture's design. Ultimately the design of any dental implant is dictated by its clinical success. Consequently, variations in the basic design of root form dental implants is limited.

Figure 1:
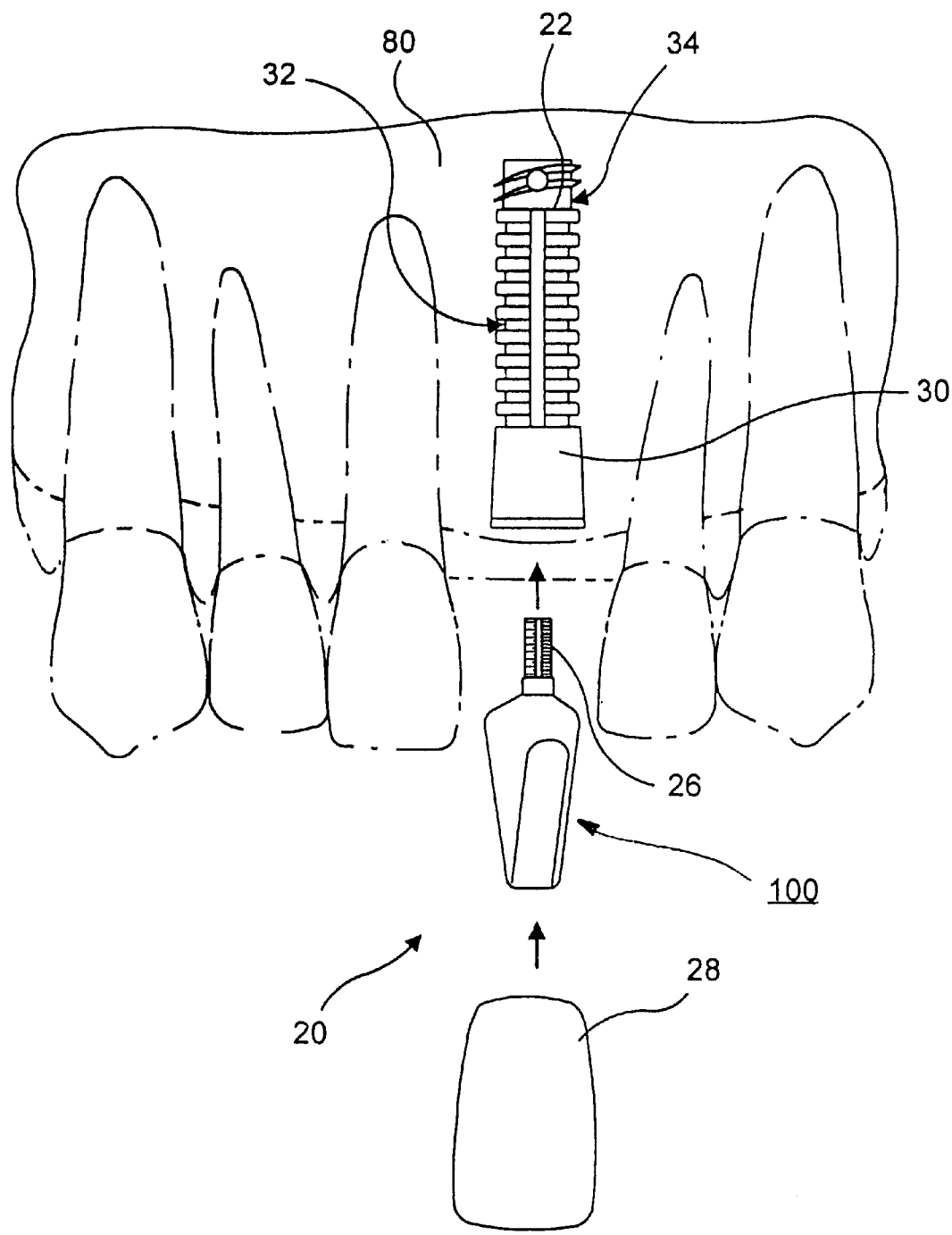
FIG. 1 is an exploded view of a representative prior conventional dental implant with the implant shown placed in the upper jaw bone.

FIG. 1 illustrates a representative conventional dental implant. This conventional dental implant 20 comprises a cylinder like member 22 having internal threads (not shown) for receiving a post 26 which supports a dental prosthesis such as, for example, a crown 28, a bridge or dentures. The cylinder like member comprises a neck portion 30 for connection with the post 26, a body portion 32 and an apex portion 34. In one exemplary embodiment of the present invention, the three component combination distraction dental implant device includes a two component externally smooth or threaded, stepped or tapered portion with round ends made of, such as, for example, implant grades of titanium or other material that performs effectively in implant usage. The external surface of the, presently preferably cylinder like, combination distraction dental implant may be smooth, roughened or coated with bone augmentation materials (hydroxyapatite, bone morphogenic proteins, titanium plasma spray, microspheres, sintered pores, selective surface combinations, etc.). The cylinder like portion of the combination distraction dental implant is separated horizontally, dividing the cylinder like portion of the combination distraction dental implant into two components, an apical component and a coronal component. The apical component of the implant may be modified to contain through and through ports, such as, for example, in a x-fashion or a y-fashion port configuration or two (2) holes through and through to allow for osseous incorporation. The apical and the coronal components, presently preferably, contain internal threads, or equivalent structure, into which a connecting component or an expansion component is operatively placed. The internal structure of the apical and the coronal components are adapted to operatively cooperate with the expansion component such that (1) at a minimum, the two components are operatively connected together and (2) the distance between the apical component and the coronal component is selectively varied.

When initially used, the connecting component is advanced into the two separable apical and coronal components by rotating, for example, the connecting component in a clockwise direction. As the connecting component is advanced into the coronal component and then into the apical component of the combination distraction dental implant, the body of the connecting component cooperates with the internal structure of the coronal component and one end of the connecting component operatively engages the internal structure of the apical component and effectively connects the two components together.

When the two components having the initial connecting component operatively positioned therein have become sufficiently integrated with the bone, the initial connecting component is removed and replaced with a first expansion component for causing separation between the apical and coronal components thereby expanding a surgically created distraction gap in the bone. Since, when properly placed in a patient's bone, the apical and coronal components become integrated, fused intra-osseously to the bone, separating these two components expands the distraction gap previously made in the bone proximal to the separation point between the two components. The separation of the components is dependent upon the cuts in the bone. If the bone is cut perpendicular to the horizonal cut in both directions, then the components will move apart, as in a sinus lift. If the bone is cut perpendicular to the horizonal cut in only one direction, then only the component most proximal the perpendicular cuts will move.

Both the initial connecting component and the expansion component are designed to be removable from a position connecting the apical and the coronal components, such as, for example, by reversing the direction of rotation. Once removed, the expansion component may be replaced with a longer expansion component, allowing for incremental distraction osteogenesis, or by an abutment for receiving a crown, once sufficient bone has been regenerated to support an optimal implant.

In any event, any one of the plurality of possible sized expansion components are operative to both connect and controllably separate the two separable components of the combination distraction dental implant and provides for the controllable separation of the separable apical and the coronal components during the distraction process. Upon completion of the distraction, the expansion component is replaced by the abutment which becomes incorporated into the bone during healing.

In one representative surgical approach, the combination distraction dental implant device is placed by making an incision along the crest of dental ridge exposing the underlying bone. Using sequentially sized drills, an osteotomy is created in the planned implant placement site. The osteotomy is sized such that the cylindrical distraction implant will fit with a friction fit. A tap drill may also be utilized to tap the bone site to receive the threaded type of distraction implant. The appropriately sized three component combination distraction dental implant is then placed and the incision is closed, with either the top of the initial connecting component extending through the soft tissue or covered by the soft tissue, the cap being flush with the surface of the bone. The combination distraction dental implant is then allowed to heal and become integrated into the bone.

If a two-stage implant procedure was determined appropriate, during Phase II, uncovering, the buccal portion of the bone is exposed. Next in both the one-stage and the two-stage procedures, osseous integration of the combination distraction dental implant is verified visually, tactilely and radiographically, as appropriate. In one presently preferred method, using radiographs, a corticotomy is created in the buccal bone at the level of the combination distraction dental implant separation site i.e., the position where the apical component and the coronal component are contiguous. The buccal cortex is scored/cut at the same horizonal level. Two vertical bicortical osteotomies are then created at the limit of the edentulous space, the area to be expanded. The incision is closed with the initial distraction connecting or expansion component extending intra-orally. After a latency period and after replacing the initial connecting component, if used, with an expansion component, the distraction expansion component is activated separating the distraction gap, i.e. the gap between the apical component and the coronal component. After adequate bone height is achieved, the last of the plurality of possible sized expansion components is removed and replaced with an abutment which acts as the basis for a prosthesis such as, for example, a crown, a bridge or dentures.

In one specific method of the present invention, the bone site for the combination distraction dental implant is created and the three component combination distraction dental implant placed. After the combination distraction dental implant has integrated into the bone, the distraction implant is surgically approached. A bone cut is made at the level of the planned distraction gap. The new bone cut is allowed a period of initial healing, and the distraction process is then initiated. This distraction activation can be coupled with (Stage II) uncovering of three component dental implant. As the gap between the apical and the coronal components of the combination distraction dental implant is advanced, the distraction gap is expanded providing for new bone formation. Once the desired amount of new bone growth has been achieved, an abutment replaces the last expansion component of the three component combination distraction dental implant and the apical and the coronal components with the abutment connecting them together is allowed to heal in position.

The following is a specific representative example of the application of the combination distraction dental implant methods and device of the present invention to the science and technology of dental implants. It is believed that most, if not all, current dental implants could be modified, in accordance with the present invention, to allow for the application of the additional distraction as long as the components of the combination distraction dental implant are sufficiently strong to withstand the loads and to effectively distribute the loads from the combination distraction dental implant to the bone.

As shown in FIGS. 2 and 3, one specific, presently preferred, embodiment of the combination distraction dental implant of the present invention is generally designated by the numeral 40 and comprises three components including a two component 42, 44, presently preferably, externally threaded cylinder like portion 46 and at least one initial connecting component 48 or one of a plurality of expansion components 48a, 48b for cooperating with the two components 42, 44 an apical component 44 and a coronal component 42 for operatively connecting and for controllably separating the two components.

The two components 42, 44 presently preferably, are about four (4.0) mm in diameter and combined are about eight (8.0) mm in length, and are made of, presently preferably, commercially pure Grade IV titanium (other metals, metal alloys or metal substances could be used as long as they meet or exceed the parameters for material used in dental implantology). The outer surface of both components of the cylinder like portion of the present invention can be conventionally covered/roughened with a surface coating extending about one (1.0) mm to about two (2.0) mm from the superior aspect of the combination distraction dental implant along the entire length of both components 42, 44. The two components 42, 44 of the combination distraction dental implant 40 are, presently preferably, cylinder like, and having, presently preferably, conventionally externally threaded, with the, presently preferably, clockwise treads starting about two (2.0) mm from the superior aspect of the combination distraction dental implant along the entire length. The apical component 44 of the combination distraction dental implant includes conventional means 50 for enhancing integration with the bone and for reducing rotation of the implant once integrated with the bone. One example, and the presently preferred means, is three oblong apical vents 52, 54, 56 about one (1.0) mm in diameter located about one half (0.5) mm superior to the end of the apical component 44 of the two components of the combination distraction dental implant 40.

The two components 42, 44 have a combined hollow portion 60 extending from the superior surface for about six (6.0) mm of the total about eight (8.0) mm length of the two components 42, 44 (completely throughout the about four (4.0) mm length of the coronal portion 42 and about two (2.0) mm into the upper portion of the apical portion 44). The hollow portion 60 is stepped with the apical portion, about a two (2.0) mm portion, having about a two (2.0) mm diameter and the coronal portion, about a four (4.0) mm portion having about a three (3.0) mm diameter. The about two (2.0) mm superior, coronal, portion 62 of the hollow inner portion 60 has a hexagonal configuration, with the coronal portion about one half (0.5) mm flared outward producing a knife edge junction. The remaining inner portion of the about two (2.0) mm long portion, of the about three (3.0) mm wide portion is round, with, presently preferably, clockwise threads. The hollow about two (2) mm diameter portion 61 of the apical component 44 is round, with, presently preferably, clockwise threads.

Figure 4:
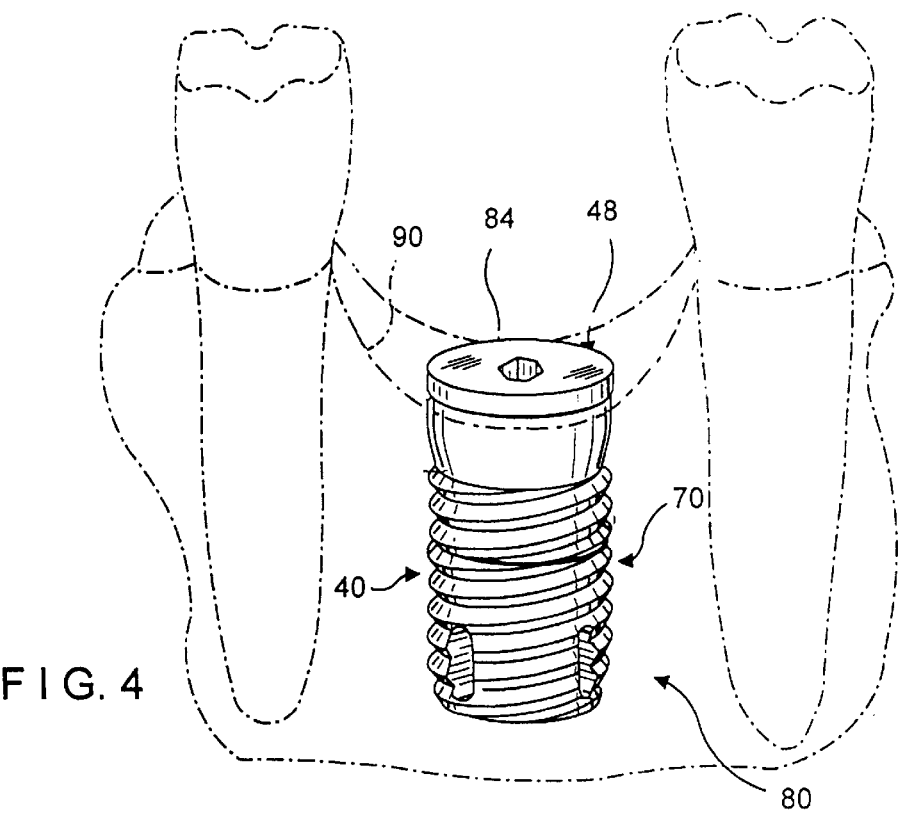
FIG. 4 is a perspective view of the representative combination distraction dental implant of the present invention shown after initial placement in an area of the jaw requiring additional bone.

Prior to, during and after initial placement, the horizontal interface between the two about, four (4.0) mm long components 42, 44 has no noticeable gap (See FIG. 4). This interface may be smooth or have interlacing or interlocking complimentary locking members on the facing surfaces 58, 59 of the components 42, 44. Such members would prevent rotation and torsion at the interface during the healing process and before the components become integrated with the bone.

Figure 8A:
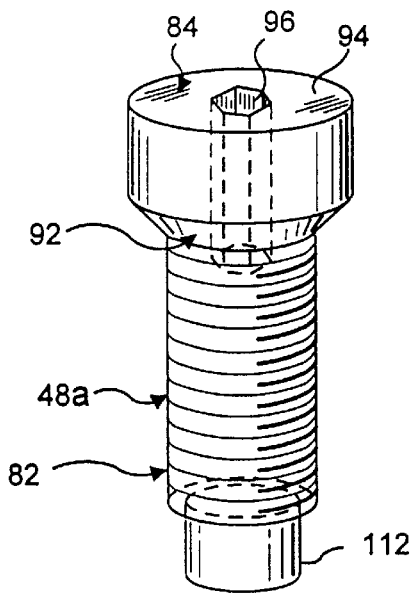
FIG. 8A is a perspective view of one representative expansion component of a plurality of different size expansion components usable with the combination distraction dental implant of the present invention.
Figure 8B:
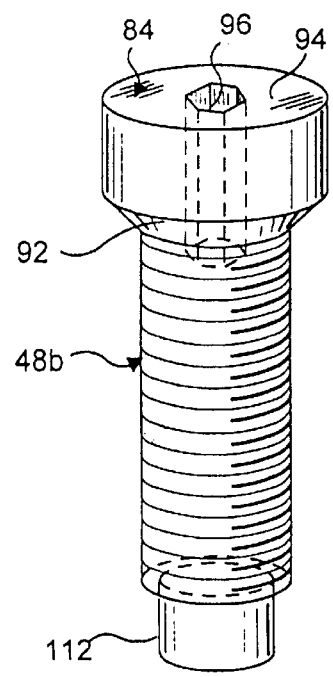
FIG. 8B is a perspective view of another representative expansion component of a plurality of different size expansion components usable with the combination distraction dental implant of the present invention.

As mentioned above, the combination distraction dental implant device 40 also includes one of the plurality of incrementally sized expansion components 48a, 48b, as shown in FIGS. 8A and 8B, for operatively connecting the two components 42, 44. As described above, the expansion component provides for separation between the above described two components 42, 44 to form a distraction gap 70, once the two components 42, 44 connected by the initial connecting component 48 are properly integrated with the bone 80. (See FIGS. 4–6)

As illustrated in FIGS. 8A, and 8B, the expansion component preferably comprises one of a plurality of separate interchangeable members 48a, 48b of varying lengths each having means for separating the two components 42, 44. The end portion 112 of the interchangeable expansion components 48a, 48b must be, of necessity, rotatable in the hollow portion 61 of the component 44, as will be discussed in detail below. The plurality of expansion components 48a, and 48b in one exemplary example, comprise separate members of about five (5.0) mm 48a, about ten (10.0) mm 48b, about thirteen (13.0) mm (not shown), about fifteen (15.0) mm (not shown), and about 18.0 mm (not shown) in length, presently preferably, made of commercially pure titanium or equivalent. Each expansion component is, presently preferably, T shaped with a threaded vertical portion 82 and a smooth superior cap portion 84. The vertical portion 82 is about two (2.0) mm in diameter with threads operatively corresponding to the internal threads of the two components 42, 44 of the distraction implant device 40 and for cooperation therewith. The height of the threaded portion has varying lengths, such as, for example, about four and one half (4.5) mm for the about five (5.0) mm expansion component, about eight (8.0) mm for the about ten (10.0) mm expansion component, about eleven (11.0) mm for the about thirteen (13.0) mm expansion component, about thirteen (13.0) mm for the about fifteen (15.0) mm expansion component, and about sixteen (16.0) mm for the about eighteen (18.0) mm expansion component.

The initial connecting component 48, and the final abutment component 100 each have a threaded end portion 110 for interaction with the hollow portion 61 of the apical component 44. The end portion 112 of the interchangeable expansion components 48a, 48b must be, of necessity, rotatable in the hollow portion 61 of the component 44 because, as the expansion component is rotated the expansion component 48a must not be fixedly connected to the apical component 44 in such a way as to prevent the end 112 from freely rotating in the apical component 44 as both the apical component 44 and the coronal component 42 remain rotationally fixed in the bone as the gap between the two components 42, 44 is increased axially by the interaction of the external threads of the expansion component 48a, 48b with the internal threads of the coronal component 42. Other conventional means for maintaining the rotatability of the end portion 112 in the hollow portion 61 would be acceptable.

The key concept is that the apical component 44 and the coronal component 42 remain stationary in the bone and rotational movement of the expansion component 48a, 48b, provided by, such as for example, the interaction of the threads of the expansion component with the internal threads of the coronal component 42, provide for the separation of the coronal component 44 and the apical component 42. Specifically, during the rotation of the expansion component after the end 112 of the expansion component 48a is contiguous with the bottom surface 63 of the apical component 44, the end component 112 freely rotates within the hollow portion 61.

The superior aspect, cap portion 84, of the initial connecting component 48 (see FIG. 2) is, presently preferably, about four (4.0) mm in diameter and either about one (1.0) mm high when unexposed or about three (3.0) mm high when exposed for the five (5.0) mm long component or about two (2.0) mm high for the remaining above described expansion components.

When seated, the about one (1.0) mm cap of the initial connecting component 48 sits flush with the edge of the combination distraction dental implant, while the about three (3.0) mm cap extends beyond the edge of the combination distraction dental implant 40 through the mucosa 90, intraorally (See FIGS. 4–7). The about two (2.0) mm cap has concentric lines spaced about 1.0 mm apart along the entire length of the cap. The superior aspect 92 of the cap is tapered inward along the about one half (0.5) mm of the one (1) mm height to correspond to the internal taper of the superior aspect/knife edge of the combination distraction dental implant 40. The top, superior surface 94 of the expansion component cap has about a one (1.0) mm diameter, hexagonal shaped aperture 96, about two (2.0) mm in depth. This aperture 96 provides the mechanical access to remove the initial connecting components 48 and to both place and remove a selected one of a plurality of the expansion components 48a, 48b from its connecting position between the two components 42, 44 and to activate the distraction process via a corresponding L or T shaped hexagonal key (not shown), of about one (1.0) mm diameter, presenting preferably, made from stainless steel, by causing separation of the two components 42, 44 of the combination distraction dental implant 40, as will be described more fully below.

Figure 8C:
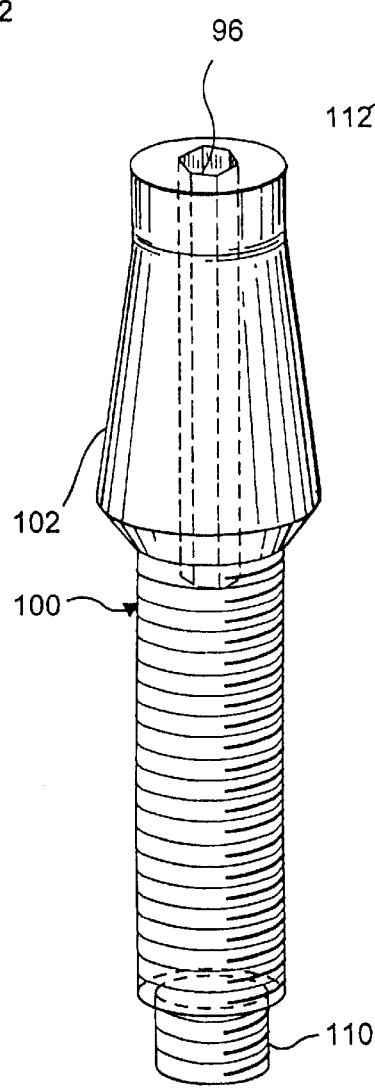
FIG. 8C is a perspective view of a representative abutment usable with the combination distraction dental implant of the present invention.

As shown in FIG. 8C, the abutment 100, for final connecting of the two components 42, 44, for being integrated with the bone and for attaching the prosthesis such as, for example, a crown 28, a bridge or dentures (FIG. 1) will now be described. The abutment 100 has essentially the same dimensions of the expansion components 48a, 48b but the overall length and the cap portion 84 as well as the end 110 most remote from the cap are necessarily altered. The cap portion 102 of, such as, for example, the crown attaching expansion component or abutment 100 is, in its presently preferred configurations, about six (6.0) mm high and about four (4.0) mm wide at its base, extending upward with no more than an about twenty-three (23) degree taper. From the widest aspect, the cap 102, presently preferably, tapers inward about two (2.0) mm to form a taper that provides for a friction fit with the internal knife edge taper of the superior portion of the combination distraction dental implant. The cap taper meets the threaded portion at about a right angle. The abutment cap 102 has the same about one (1.0) mm diameter hexagonal access aperture in its superior surface. This final abutment component is the component utilized as the base for the prosthesis such as, for example, a crown 28, a bridge or dentures after sufficient bone growth through distraction osteogenesis has been generated by the controlled separation of the two components 42, 44 by the expansion component. The cap portion 102 may also be configured as a ball, bar, magnet or any abutment, as is known in the art. The end 110 of the abutment 100 must be operative to interlock with the component 44 such that during bone integration, the two components 42, 44 remain fixedly connected.

As illustrated in FIGS. 4–7, in one presently preferred method for the distraction of bone using the combination distraction dental implant 40 described above, the combination distraction dental implant 40 device is placed by making a series of osteotomies within the dentoalveolar bone in the predetermined site or area where additional bone is required. Prior to any surgical technique, proper treatment planning must be performed, including a physical examination, X-ray studies and consultation with the dentist fabricating the prosthetic crown.

Once the patient has been conventionally prepared for surgery, a local anesthetic is given and infiltrated into the surgical site. After allowing adequate time for anesthesia and vasoconstriction, incisions are made along the crest of dental ridge, in the predetermined site. The underlying bone is conventionally exposed by raising a full thickness mucoperiosteal flap with an elevator. The exposed bone is conventionally evaluated by palpitation for bone density and quality.

Using sequentially sized drills, (an acceptable set is available from Dentsply® Implant, 15821 Ventura Blvd., Ste. 420, Encino, Calif. 91436) as is presently preferred, an osteotomy is created in the planned implant placement site, it being understood that other conventional procedures could be used to create the osteotomy. First, presently preferably, about a two (2.0) mm diameter pilot drill is used to initiate the osteotomy site, such as, for example, to a depth of about eight (8.0) mm. All of the bone drilling procedures include copious amounts of irrigation, (internally and/or externally). Conventional paralleling pins of about two (2.0) mm diameter are placed into the pilot holes to ensure the proper orientation and location of the combination distraction dental implant in the bone. The osteotomy site is enlarged by utilizing progressively wider drills. The proper orientation and depth of the osteotomy site is verified by re-placing the paralleling pins. Optionally, the parallelism of the osteotomy site can be verified by X-rays. The final sized osteotomy site is completed by either utilizing the final, smooth, twist drill or by tapping in the threads corresponding to the combination distraction dental implant.

At this point, the three component combination distraction dental implant 40 of the present invention is placed (see FIG. 4) into the bone 80 manually or by use of a conventional implant drill set at slow speeds, as is known by those skilled in the art. The wound is irrigated and the incision is conventionally closed with the cap 84 being, presently preferably, covered by the gum tissue. In a one-stage implant procedure, the cap is exposed, as described above.

The three component distraction dental implant 40, presently preferably, with the initial connecting expansion component 48 is then allowed to heal and become integrated into the bone (a process that takes approximately four months).

It should be understood that it may be possible to substitute a first expansion component 48a in place of the initial connecting component 48, as long as the portion extending above the gum does not extent above the top of any adjacent tooth and as long as other medical concerns are met as appropriate.

After physical examination and X-ray evaluation are utilized to ensure osseous incorporation of the combination distraction dental implant, the top 84 or superior portion of the combination distraction dental implant is exposed during the Phase II, uncovering surgical procedure in a two-stage procedure where the implant is completely covered (not shown). In the case of a one-stage implant, the cap is not covered, as shown in FIGS. 4–7.

During either the one-stage or the two-stage procedure, local anesthetic is administered, after the patient has been prepared for surgery. Incisions are made in the gum over the site of the combination distraction dental implant (two-stage procedure). A full thickness mucoperiosteal flap is raised along the buccal portion utilizing a periosteal elevator. Osseous integration of the two component combination distraction dental implant 40 into the bone is verified visually and tactilely. Using a burr and copious amounts of irrigation, a corticotomy is placed in the buccal bone horizontally, adjacent the two components separation point (about 4.0 mm from the superior dental aspect of the combination distraction dental implant). The horizontal corticotomy, presently preferably, extends laterally about one (1.0) mm to about seven (7.0) mm beyond the margin of the two component combination distraction dental implant or as appropriate, depending upon the judgment of the surgeon.

Two vertical bicortical osteotomies are created extending from the horizontal cut to the crest of the dental ridge. This cut can also be preformed in the opposite direction, apically to allow for the sinus lift procedure, as described later. The vertical osteotomies are completed with a thin osteotome. Care is taken not to perforate the lingual periosteum or mucosa. The horizontal cut remains as a corticotomy. If the combination distraction dental implant has been placed in an area of limited bone stock, about one (1) to about two (2) millimeters, between the implant and the adjacent teeth/ nerve, then only corticotomies are performed including on the lingual.

At this point, the patient has been prepared for the process of growing new bone stock by distraction osteogenesis prior to the prosthesis such as, for example, a crown, a bridge or dentures being connected to the implant. First, if used, the initial connecting component 48 is removed and replaced by a first adjustable expansion component 48a. The incision is then closed, with the cap of the adjustable expansion component 48a extending about five (5.0) mm through the mucosa, intraorally.

The patient is educated as to the care and activation of the three component combination distraction dental implant. After allowing for a period of initial healing, a latency period (of about 5–7 days), the adjustable expansion component 48a is maneuvered, (turned) thereby separating the two components 42, 44 of the combination distraction dental implant 40 of the present invention (about 1.0 mm per day) in divided doses, as is known in the art, and thus creating and widening the distraction gap 70 in the bone.

The patient is educated to make the adjustment necessary to increase or widen the gap 70 each day. Thereafter, the patient is seen for follow-up and evaluation as appropriate. Since the plurality of expansion components 48a, 48b are incrementally sized by about five (5.0) mm, the maximal distraction gap advancement achieved by any one expansion component is about five (5.0) mm. If greater bone growth is required, the first expansion component 48a can be removed and replaced by the next longer sized expansion component 48b and the distraction process reinitiated, to achieve further bone regeneration, as above (See FIGS. 4–7).

If an initial expansion component 48a was used instead of the initial connecting component 48, the actuation process, after healing, is followed, as described above.

Since the typical height of a natural tooth crown 111 above the gum 90 is about eight (8.0) mm, in order to properly function, the distal or cap end of the expansion component 48a should not extend above the level of the lowest adjacent tooth crown 111.

After sufficient bone height (about 5 mm to about 15 mm) is achieved, the distraction process is halted and the last adjustable expansion component is removed and replaced with the abutment 100. However, since the new bone is still relatively weak and incompletely ossified, a period of about four to about six weeks is required before the fabrication and installation of the final prosthesis such as, for example, a crown 28, a bridge or dentures. Additionally during this period, the abutment 100 now connecting the two components 42, 44 of the combination distraction dental implant becomes incorporated with the bone thereby increasing the rigidity of the installed combination distraction dental implant device 40 of the present invention.

Figure 5:
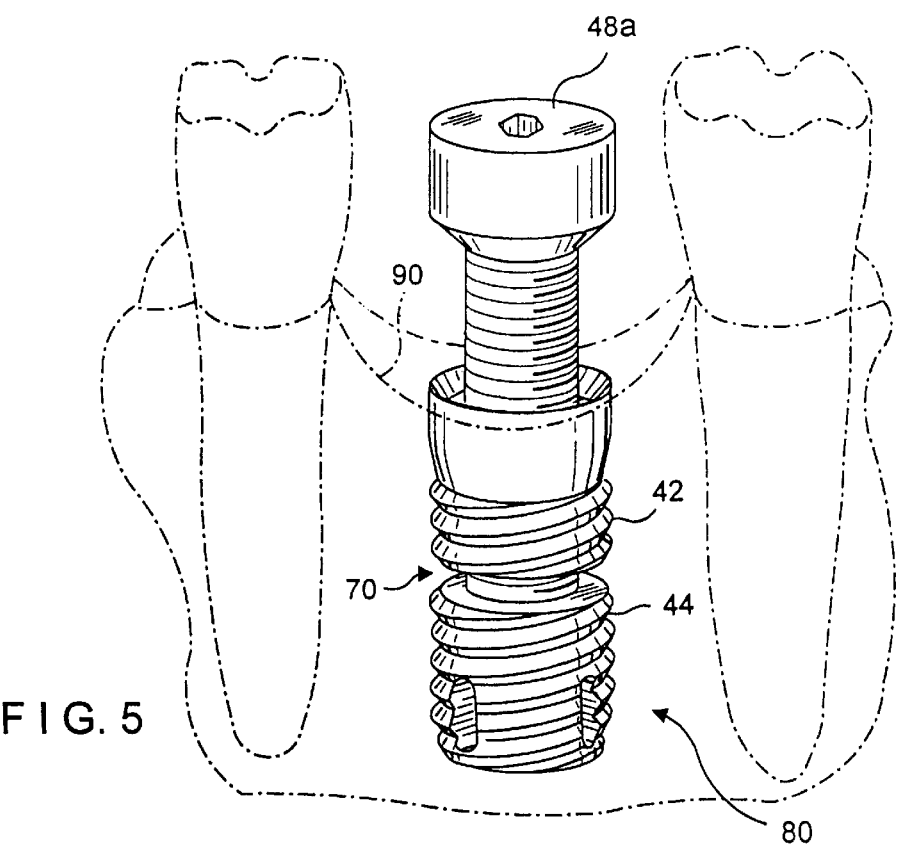
FIG. 5 is a perspective view of the representative combination distraction dental implant of FIG. 4 shown after initial placement in an area of the jaw requiring additional bone and after some bone has be generated.
Figure 6:
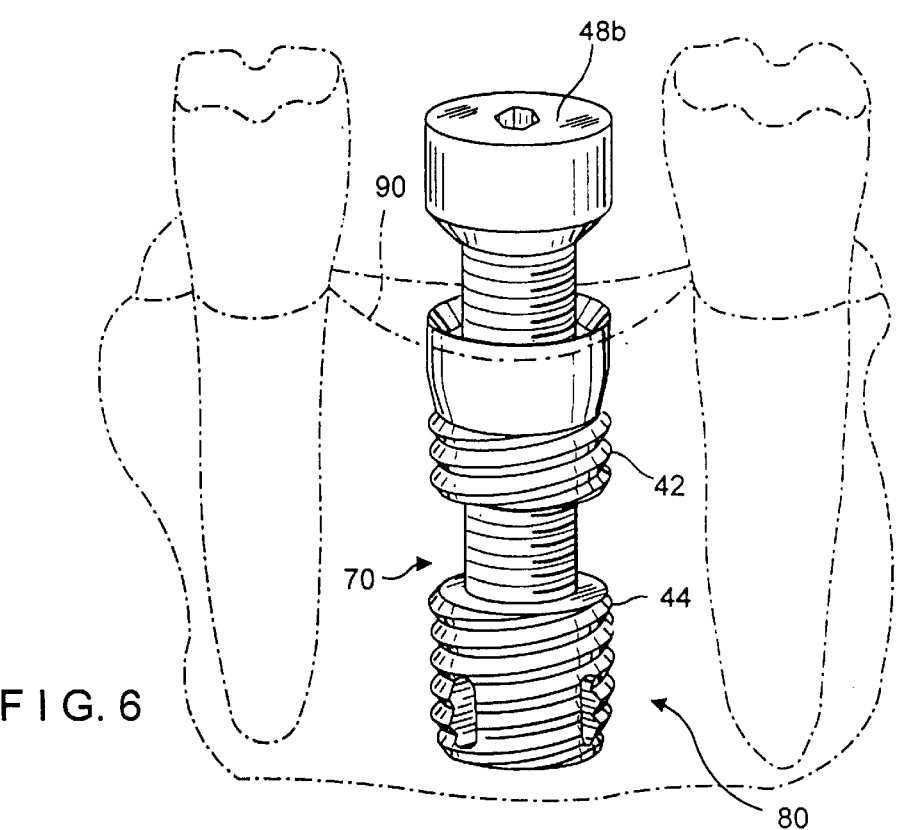
FIG. 6 is a perspective view of the representative combination distraction dental implant of FIG. 4 shown after initial placement in an area of the jaw requiring additional bone and after additional bone has be generated.
Figure 7:
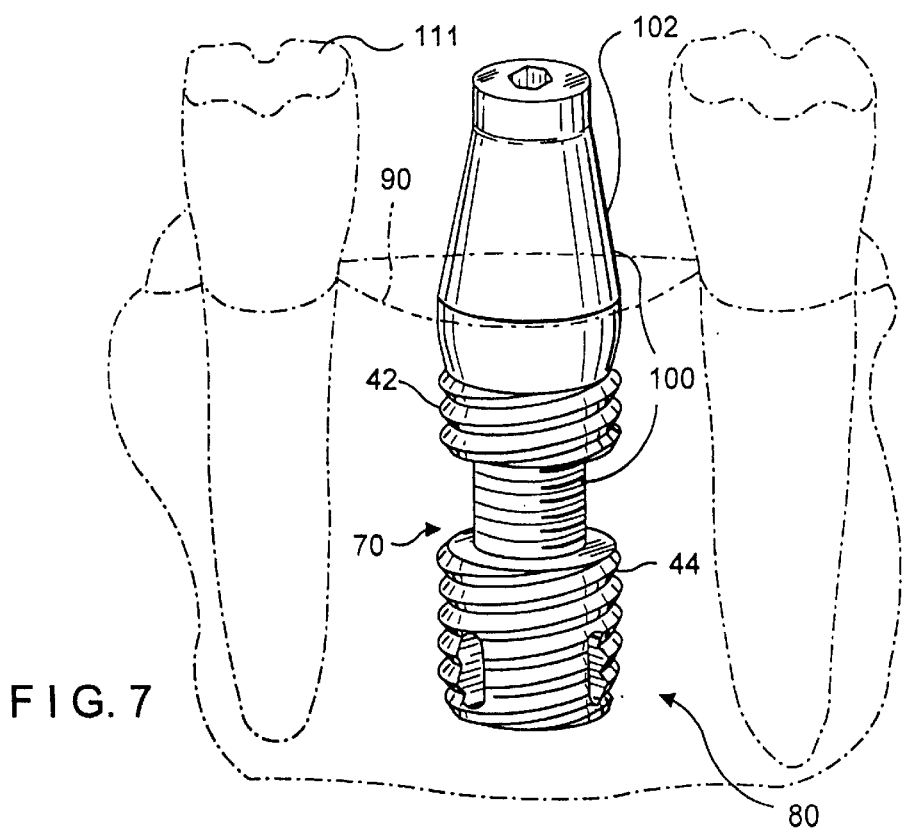
FIG. 7 is a perspective view of the representative combination distraction dental implant of FIG. 5 shown after sufficient bone has be generated to support an optimum crown.

FIGS. 4–7 illustrate the distraction process according to the present application. FIG. 4 shows the combination distraction dental implant 40 of the present invention newly installed in an area having insufficient bone to support an optimal dental implant. FIG. 5 shows an intermediate bone growth situation where some bone has been regenerated but not enough to support an optimal dental implant. Note the increased separation between the coronal 42 and apical 44 components and the increased distraction gap 70. FIG. 6 shows another intermediate bone regeneration position with FIG. 7 showing the final result with the abutment lo being positioned connecting the two components 42, 44.

As clearly illustrated in FIGS. 4–6, as the bone is regenerated and the expansion component 48a becomes nearly flush with the gum, the expansion component connecting the coronal 42 and apical 44 components is removed and replaced with the next longer of the plurality of expansion components 48b such that, presently preferably, the end extending intraorally does not extend above the adjacent teeth, a height of about five (5) millimeters.

The foregoing description illustrated one specific application of the technique and technology of distraction osteogenesis to the field of dental implants using an exemplary device and method. Since conventional dental implants have similar basic forms, it should be apparent to those skilled in the art that the potential combinations of the three component combination distraction dental implant devices is unlimited. By modifying minor details of the basic design, such as, for example, splitting the dental implant horizontally 60/40% rather than the 50/50% as described, altering the length or taper of the expansion component, changing the pitch of the screws, etc., are just a few of the unlimited possible variations.

Nevertheless, in all possible variations, the basic concept remains as described, i.e., utilizing two separate components 42, 44 connected by one of a plurality of adjustable expansion components to achieve sufficient bone generation in an area of deficient bone in order to place an optimum dental implant. Advantages of combination distraction dental implant of the present invention include providing new bone and soft tissue formation, thereby, reducing the number and morbidity of surgical procedures a patient is subjected to during the distraction as compared to the prior surgical procedures. Additionally, the three component combination dental implant described above provides for increased versatility by using a plurality of interchangeable, incrementally seized expansion components 48a, 48b to continuously adjust the distraction gap 70 during the bone regeneration process without additional surgical procedures. Consequently if more bone is required than initially anticipated, then the expansion component, and only this single component, is removed and replaced with a longer one to provide the additional bone generation until sufficient bone is generated then the last expansion component is replaced by the abutment 100.

Figure 9:
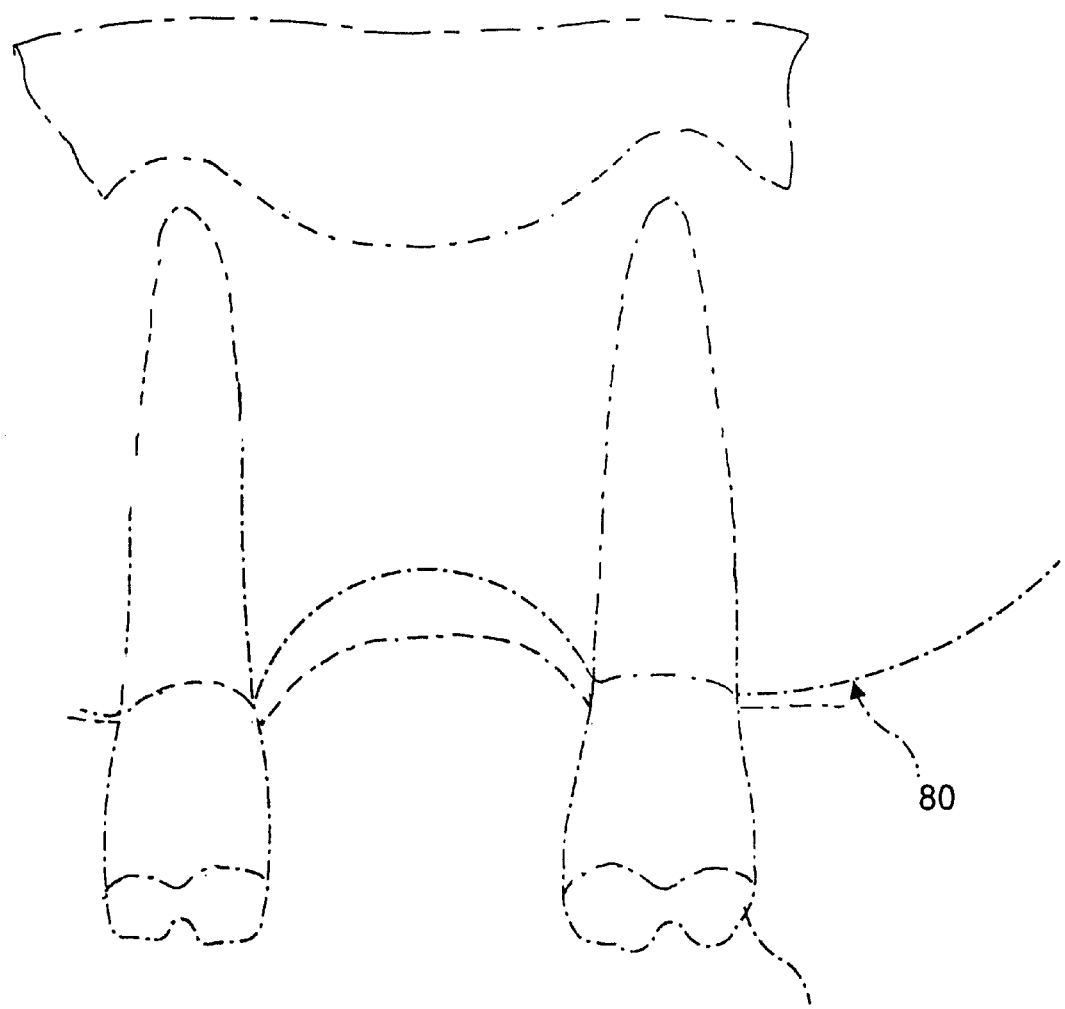
FIG. 9 is a schematic view of a maxillary sinus in an area of the jaw having diminished bone height requiring additional bone prior to the placement of an implant.

As shown in FIGS. 9–12, utilization of the device of the present invention for cases where the bone is deficient and the sinus must be elevated. As shown in FIG. 9, the device 40 of the present invention is placed in the bone 80 with the apical component 44 proximate the boundary between the bone 80 and the maxillary sinus 200.

Figure 10:
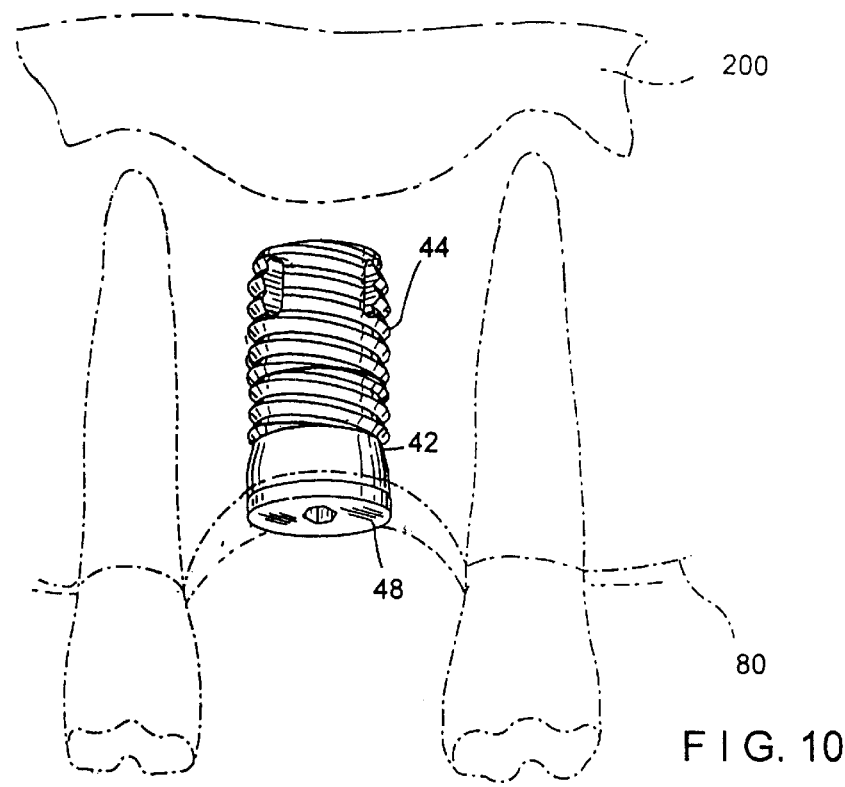
FIG. 10 is a schematic view of the representative combination distraction dental implant of the present invention shown after initial placement in an area of the jaw requiring additional bone.
Figure 11:
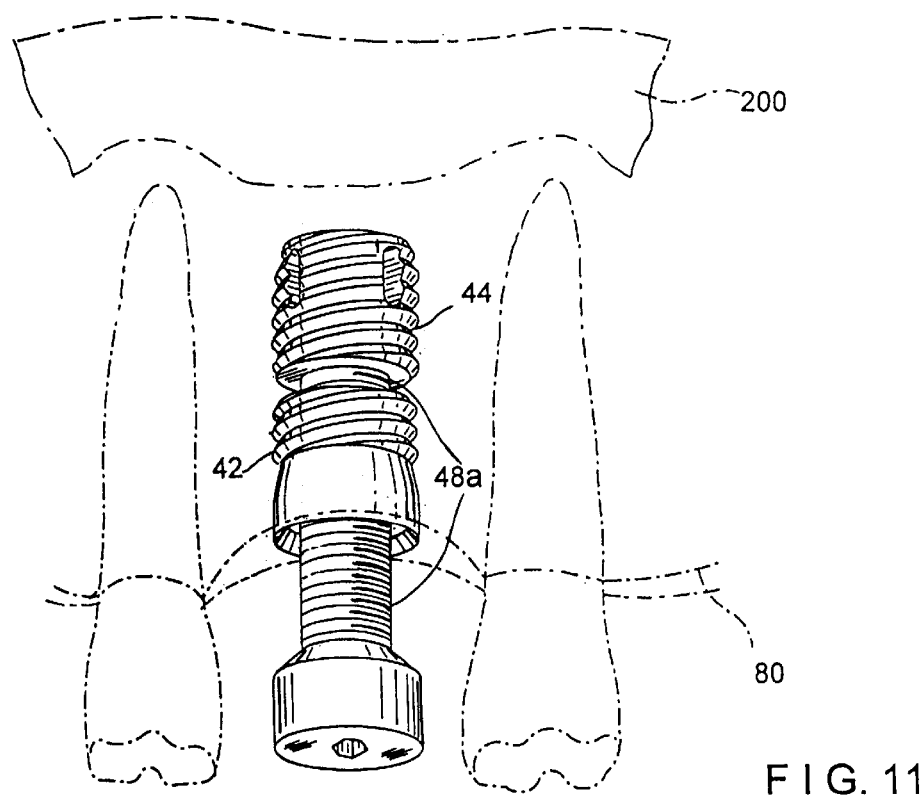
FIG. 11 is a schematic view of the representative combination distraction dental implant of FIG. 10 shown after initial placement in an area of the jaw requiring additional bone and after some bone has been generated lifting the maxillary sinus.
Figure 12:
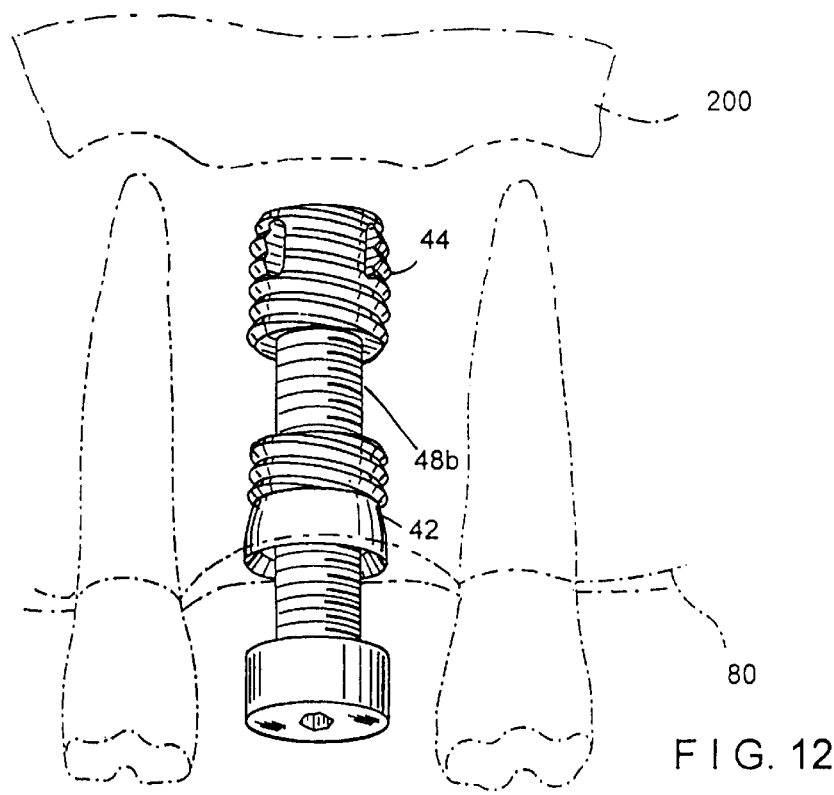
FIG. 12 is a schematic view of the representative combination distraction dental implant of FIG. 11 shown after additional bone has been generated further lifting the maxillary sinus.
Figure 13:
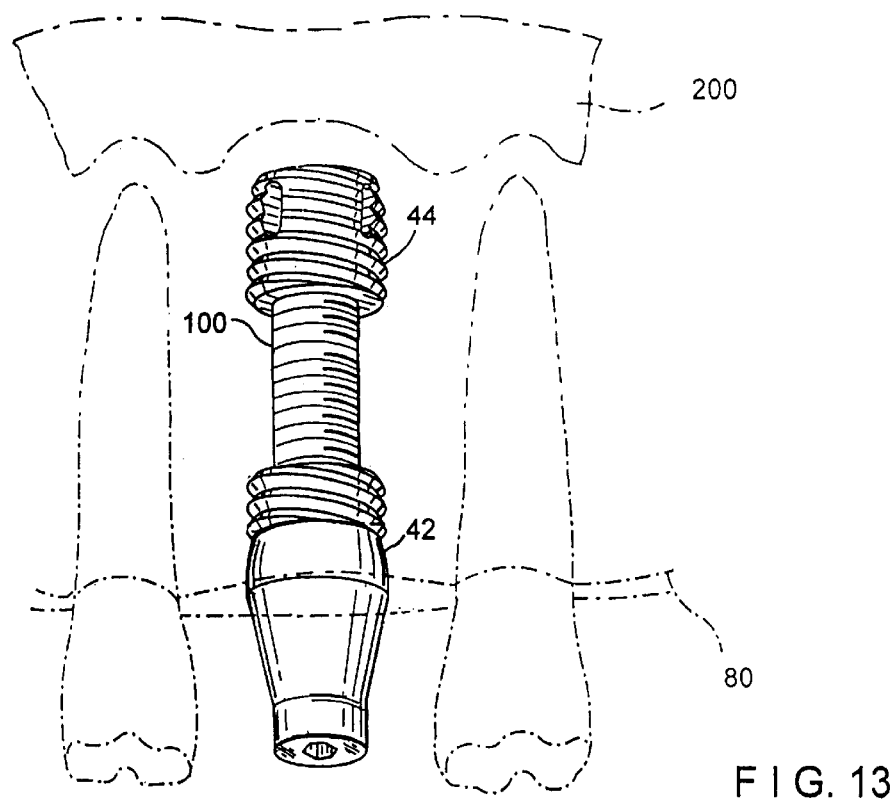
FIG. 13 is a schematic view of a representative combination distraction dental implant of FIG. 11 shown after sufficient bone has been generated to support an optimum crown and even further lifting the maxillary sinus.

FIGS. 10–12 illustrate the regeneration of the bone as the apical component 44 effectively lifts the maxillary sinus 200 in gradual phases through distraction osteogenesis by regenerating bone between the apical 44 and the coronal 42 components.

In this method, one possible approach is to have both the coronal component 42 and the apical component 44 generate bone by having the apical component 44 push toward the sinus 200 and the coronal component 42 move toward the crown of the adjacent teeth and increase the bone between the sinus and the gum. Therefore, when the force is applied to separate the two components, distraction takes place by moving both components, depending upon the bone cuts (osteotomies), as previously described.

As can be seen from the drawings, it is believed possible to elevate the maxillary sinus while generating sufficient bone to provide the equivalent of the conventional bone graft system of the prior art. One representative prior method and apparatus for lifting a descendent portion of the maxillary sinus is disclosed in U.S. Pat. No. 4,682,951, the disclosure of which is herein incorporated by reference.

Thus, it can be seen that the new combination intraossoeus dentoalveolar distraction osteogenesis implant and method of using includes a new three component device which reduces the number of surgical procedures required to place a dental implant in an area initially having insufficient bone stock to support the optimal implant and is more aesthetically pleasing during the actual distraction process as compared to prior devices and methods.

It should be clear to those skilled in the art that the above concept of a three component distraction device with interchangable expansion components is not limited to use as a dental implant and could be used as a general distraction device in the maxillofacial region, for example, by externally attaching the coronal component and the apical component to appropriate areas of a bone by connecting means, such as, for example, pins, screws, rods, titanium discs, etc., as known by those skilled in the art. When attached external to the bone and soft tissue (extra mucosal), the same distraction principles would apply including the variable size interchangeable connecting components.

In fact, a plurality of interchangeable, incremental devices, each device comprising a first component operatively, removably connected to a first bone connecting means, a second component operatively, removably connected to a second bone connecting means and a guide means operatively connecting the first and second components could be positioned external to the skin or soft tissue of the mouth intraorally to effectuate distraction of bone, such as, for example, the mandible. Such a device would have the advantage of being initially much smaller, resulting in considerable increased patient comfort because it is not necessary for the initial device to be the length of the final distance to be distracted, as with currently used devices, such as, for example, the devices shown in FIGS. 11 and 14 in the article entitled "Osteodistraction" mentioned above. Also, the device causes less tissue displacement (lips) thereby reducing aesthetic concerns and is better tolerated by the patient. Finally, the device is smaller, due to its incremental construction, and, thus, easier to remove at each intermediate position and at the end of the distraction process.

Changes and modifications in the specifically described embodiments and methods can be carried out without departing from the scope of the invention which is intended to be limited only by the scope of the appended claims.

What is claimed is:

1. A combination distraction dental implant comprising:
   a hollow coronal component;
   an apical component, said coronal component movable with respect to said apical component, said apical component having at least one surface initially contiguous with at least one surface of said hollow coronal component; and
   at least one expansion component having:
   (a) mechanically connecting means for securing said hollow coronal component to said apical component, and
   (b) expansion gap means for controllably expanding in situ the distance between said contiguous surfaces of said hollow coronal component and said apical component.

2. The combination distraction dental implant of claim 1 wherein the combined hollow coronal component and the apical component are about 4.0 mm in diameter and about 8.0 mm in length.

3. The combination distraction dental implant of claim 1 wherein the hollow coronal component and the apical component are each made of commercially pure Grade IV titanium.

4. The combination distraction dental implant of claim 1 wherein the outer surface of both the hollow coronal component and the apical component is covered with a surface coating extending about 1.0 mm from the superior aspect of the hollow coronal component along the entire remaining length of both components.

5. The combination distraction dental implant of claim 1 wherein the interior surfaces of the hollow coronal component and the interior surfaces of the apical component are threaded.

6. The combination distraction dental implant of claim 5 wherein the treads are orientated clockwise starting about 2.0 mm from the superior aspect of the hollow coronal component.

7. The combination distraction dental implant of claim 1 wherein the apical component further comprises:
   means for reducing rotation of the implant once integrated with the bone.

8. The combination distraction dental implant of claim 7 wherein the rotation reducing means comprises:

three oblong apical vents about 1.0 mm in diameter located about 1.0 mm superior to the apical component.

9. The combination distraction dental implant of claim 1 wherein the hollow portion of the coronal component extends completely therethrough and the apical component has a hollow portion extending about one half of the way therethrough.

10. The combination distraction dental implant of claim 9 wherein the combined hollow portions are stepped with the apical portion, about a two (2.0) mm portion, having about a two (2.0) mm diameter and the coronal portion, about a four (4.0) mm portion, having about a three (3.0) mm diameter.

11. The combination distraction dental implant of claim 10 wherein the about two (2.0) mm superior, coronal, portion of the hollow inner portion has a hexagonal configuration, with the apical portion about one half (0.5) mm flared outward forming a knife edge junction and the remaining inner portion of the about two (2.0) mm long portion, of the about three (3.0) mm wide portion is round, with clockwise threads.

12. The combination distraction dental implant of claim 1 wherein the hollow about two (2) mm diameter portion of the apical component is round, with clockwise threads.

13. The combination distraction dental implant of claim 1 wherein the hollow coronal component and the apical component are each about 4.0 mm long with the interface between the two components having no noticeable gap therebetween.

14. A method for the distraction of bone comprising the steps of:
   providing a three component distraction device including a hollow coronal component, an apical component and a connecting component or a first expansion component;
   placing the combination distraction device in a predetermined site where bone regeneration is required;
   allowing the combination distraction device to become integrated into the bone;
   ensuring that osseous incorporation of the combination distraction device into the bone has been accomplished;
   performing a corticotomy in the buccal bone at the level of the contiguous surfaces of two of the three components of the combination distraction device to form a distraction gap;
   educating the patient as to the care and activation of the three component combination distraction device;
   after allowing for a period of initial healing, maneuvering the connecting component thereby separating the coronal component and the apical component to widen the distraction gap in the bone.

15. The method of claim 14 further comprising the step of:
   cutting the buccal cortex vertically to create two vertical bicortical osteotomies extending from the horizontal cut to about the crest of the dental ridge.

16. The method of claim 15 further comprising the step of:
   completing the vertical osteotomies with a thin osteotome.

17. The method of claim 14 further comprising the step of:
   educating the patient to make the adjustment necessary to widen the gap each day.

18. The method of claim 14 further comprising the step of:
   closing an incision made prior to placing the three component distraction device such that initial connecting components extend through the mucosa, initially.

19. The method of claim 14 further comprising the steps of:
   providing a plurality of expansion components, each being incrementally sized by about 5.0 mm.

20. The method of claim 19 further comprising the steps of:
   if greater bone growth is required after the maximal distraction gap advancement achieved by the first expansion component, removing the first expansion component.

21. The method of claim 20 further comprising the steps of:
   replacing the first expansion component with the next longer sized expansion component; and
   reinitiating the distraction process such that further bone regeneration is achieved.

22. The method of claim 21 further comprising the steps of:
   after sufficient bone growth is achieved, removing the last expansion component; and
   installing an abutment.

23. The method of claim 22 further comprising the step of:
   allowing sufficient time for the new bone to completely ossify.

24. The method of claim 23 further comprising the step of:
   installing the final dental prosthesis.

25. The method of claim 14 wherein the three component distraction device comprises:
   a hollow coronal component;
   a partially hollow apical component initially having at least one contiguous surface with at least one surface of the hollow coronal component; and
   at least one connecting component for:
      (a) operatively connecting the hollow coronal component and the partially hollow apical component, and
      (b) controllably expanding the distance between the contiguous surfaces of the hollow coronal component and the partially hollow apical component.

26. The method of claim 14 wherein the distraction gap in the bone is widened from about 0.5 mm to about 2.0 mm per day.

27. An in-situ, combination distraction and dental implant system comprising:
   a) an apical member having a top surface;
   b) a coronal member comprising internal threads and a bottom surface, said bottom surface of said coronal member facing said top surface of said apical member; and
   c) a rod-like connecting and distraction member, comprising a first set of external threads matingly engageable with said internal threads of said coronal member and rotation enabling means for facilitating mechanical incremental rotation of said connecting and distraction member with respect to said coronal member,
   said system further comprising vertical movement limit means for preventing relative vertical movement beyond a predetermined point of said connecting and distraction member with respect to said apical member as said connecting and distraction member is rotated with respect to said coronal member, such that incremental rotation of said connecting and distraction member causes said coronal member to vertically separate from said apical member and create a correspondingly-sized vertical gap between said top and said bottom surfaces for distraction osteogenesis.

28. A combination distraction and dental implant system as claimed in claim 27 wherein said apical member is provided with exterior surface means for enhancing integration with bone and for inhibiting rotation of said apical member with respect to bone after commencement of distraction osteogenesis.

29. A combination distraction and dental implant system as claimed in claim 28 wherein said exterior surface means comprises at least one of a) external surface irregularities and b) vents located on the external surface of said apical member and extending inwardly into said apical member.

30. A combination distraction and dental implant system as claimed in claim 29 wherein said external surface irregularities comprise screw threads.

31. A combination distraction and dental implant system as claimed in claim 27 wherein said apical member is cylindrical.

32. A combination distraction and dental implant system as claimed in claim 27 wherein said apical member provides said vertical movement limit means comprising a blind bore defining a contact surface for the distal end of said connecting and distraction member.

33. A combination distraction and dental implant system as claimed in claim 32 wherein two or more connecting and distraction members are provided of different length.

34. A combination distraction and dental implant system as claimed in claim 27 further comprising a rod-like initial connecting member having exterior threads at its distal end and said apical member comprises a set of internal screw threads matingly engageable with said exterior threads of said initial connecting member.

35. A combination distraction and dental implant system as claimed in claim 34 wherein said initial connecting member is further provided with a second set of external threads which matingly engage with said internal screw of said coronal member.

36. A combination distraction and dental implant system as claimed in claim 27 wherein said connecting and distraction member comprises a prosthesis securing means for support of a dental prosthesis.

37. A combination distraction and dental implant system as claimed in claim 36 further comprising a dental prosthesis.

38. A combination distraction and dental implant system as claimed in claim 36 wherein said prosthesis securing means comprises a shaped keyhole.

39. A combination distraction and dental implant system as claimed in claim 36 wherein said prosthesis securing means and said rotation enabling means comprise a shaped keyhole.

40. A combination distraction and dental implant system as claimed in claim 36 wherein said system further comprises a cap and threaded-segment portion securable to said prosthesis securing means of said coronal member.

41. A combination distraction and dental implant system as claimed in claim 40 wherein said threaded-segment portion is provided with external screw threads which matingly engage with said internal threads of said coronal member and said cap portion is provided with keyhole shaped means for facilitating rotation and securing of said cap portion to said coronal member.

42. A combination distraction and dental implant system as claimed in claim 27 wherein said external threads of said connecting and distraction member do not extend along its full length.

43. A combination distraction and dental implant system as claimed in claim 27 wherein said coronal member is cylindrical.

44. A combination distraction and dental implant system as claimed in claim 27 wherein said coronal member is provided with exterior surface means for enhancing integration with bone and inhibiting rotation of the coronal member with respect to bone after commencement of distraction osteogenesis.

45. A combination distraction and dental implant system as claimed in claim 44 wherein said exterior surface means comprises external screw threads.

46. A combination distraction and dental implant system as claimed in claim 27 further comprising an initial connecting member formed of two sections, a first set of external threads being on the first of said two sections and said second section being of a different diameter than said first of said two sections.

47. A combination distraction and dental implant system as claimed in claim 46 wherein said apical member is provided with internal threads and said second section of said initial connecting member is provided with a second set of external threads which matingly engage with said internal threads of said apical member.

48. A combination distraction and dental implant system as claimed in claim 27 wherein two or more connecting and distraction member are provided of different length.

49. A combination distraction and dental implant system as claimed in claim 27 wherein said coronal member is cylindrical and said internal threads define an axial bore extending along a central longitudinal axis of said coronal member.

50. A combination distraction and dental implant system as claimed in claim 49 wherein said connecting and distraction member extends through said coronal member and at least partially into a blind bore of said apical member.

51. A combination distraction dental and implant system as claimed in claim 27, wherein said vertical movement limit means comprises a blind bore of said apical member defining a contact surface and the distal end of said connecting and distraction member, the length of said connecting and distraction member being sufficient to extend through said coronal member and into contact with said contact surface of said apical member.

52. A combination distraction and dental implant system as claimed in claim 27 wherein said rotation enabling means comprises an axially-located shaped key.

* * * * *